United States Patent [19]

Newton et al.

[11] 3,946,738
[45] Mar. 30, 1976

[54] LEAKAGE CURRENT CANCELLING CIRCUIT FOR USE WITH ELECTROSURGICAL INSTRUMENT

[76] Inventors: David W. Newton, 4523 Canterbury, Boulder, Colo. 80304; John M. Adan, 3300 Martin Drive, Boulder, Colo. 80303

[22] Filed: Oct. 24, 1974

[21] Appl. No.: 517,492

[52] U.S. Cl. ...... 128/303.14; 128/303.17; 317/9 A; 317/18 D
[51] Int. Cl.² .................... A61B 17/36; A61N 3/00
[58] Field of Search..... 128/303.13, 303.14, 303.17, 128/422, 2.1 P; 317/18 D, 9 A, 9 AC

[56] References Cited
UNITED STATES PATENTS

| | | | |
|---|---|---|---|
| 3,601,126 | 8/1971 | Estes | 128/303.14 |
| 3,675,655 | 7/1972 | Sittner | 128/303.17 |
| 3,699,967 | 10/1972 | Anderson | 128/303.14 |
| 3,804,096 | 4/1974 | Gonser | 128/303.14 |

FOREIGN PATENTS OR APPLICATIONS

| | | | |
|---|---|---|---|
| 855,459 | 10/1960 | United Kingdom | 128/303.17 |

*Primary Examiner*—Ronald L. Frinks
*Assistant Examiner*—Lee S. Cohen

[57] ABSTRACT

Circuitry for cancelling leakage current is disclosed. The leakage cancelling circuit is utilized in conjunction wih the active or patient electrodes of an electrosurgical instrument used in electrosurgery. In electrosurgery, a radio frequency current is passed through a patient between an active electrode and a patient electrode with the active electrode determining the point where surgery is performed and the patient electrode being made surgically inactive by large patient contact area. Current leakage at the electrodes is caused by stray capacity to ground in an isolated system and excessive leakage from the active electrode to ground can cause surgery to be performed without a patient connection while excessive leakage from the patient electrode to ground can cause RF burns to the patient and perhaps to operating room personnel having contact with the patient. In one embodiment, current leakage is cancelled by addition of current to the patient connection in correct phase and magnitude to cancel the existing patient leakage currents, the added current being supplied through circuitry that includes a capacitor in series with the tertiary winding on the output power transformer supplying current to the active and patient electrodes. In a second embodiment, a series LC circuit is placed in parallel with the stray capacitance to cancel the same.

8 Claims, 2 Drawing Figures

LEAKAGE CURRENT CANCELLING CIRCUIT FOR USE WITH ELECTROSURGICAL INSTRUMENT

FIELD OF THE INVENTION

This invention relates to a leakage current cancelling circuit and more particularly relates to a leakage current cancelling circuit for use with an electrosurgical instrument.

BACKGROUND OF THE INVENTION

The use of electrosurgical instruments to perform electrical functions such as cutting and/or coagulation is well known. An example of such an electrosurgical instrument is shown in U.S. Pat. No. 3,699,967, issued Oct. 24, 1972 to Robert K. Anderson and entitled "ELECTROSURGICAL GENERATOR."

In this type of surgery, a radio frequency, (R.F.) current is generated at a generator and then coupled through an output power transformer and capacitors to the active and patient electrodes in the electrosurgical instrument, the electrosurgical function being performed by passing the R.F. current through a patient in contact with the electrodes. As is also well known, surgery is performed at the point where the active electrode is in contact with the patient and to this end the active electrode is normally of small size to achieve high current density at the point of contact with the patient. Since the patient electrode, however, is meant to be surgically inactive, a large area of contact with the patient is desired to thus create a low current density.

While the electrodes of the electrosurgical instrument can have the patient electrode connected with ground to thus provide a grounded output configuration, it has been found advantageous to isolate both electrodes from ground to thus establish an isolated output configuration. The isolated output configuration has been found advantageous in that power can be supplied only between the output terminals, rather than between one terminal and ground. The inability to develop power to ground alleviated a common problem in electrosurgery caused by a break in the patient connection which heretofore has been known to cause power burns at the point of ground contact with the patient. The isolated output configuration also has proved to be advantageous since the patient is not grounded and this reduces the possibility of low frequency ground-completed circuits through the patient which could result in electrocution of the patient.

A disadvantage of the isolated output configuration heretofore, however, has been due to the presence of ground-seeking R.F. leakage currents emanating from either pole of the generator. These leakages are caused by stray capacity to ground on either the active or patient side of the output circuit. Stray capacity on the active side of the output circuit can cause a current to flow between the patient connector and ground if this point is referenced near ground, while stray capacity on the patient side of the output circuit can cause currents to flow between the active side and ground.

Excessive leakage from the active side of the output circuit to ground can bring about a situation where surgery can be accomplished without a patient connection and result in severe risk of R.F. burns to the patient. Excessive leakage from the patient side of the output circuit to ground, on the other hand, can bring about a situation where the patient attains an R.F. voltage with respect to ground and this can result in R.F. burns to the patient and possibly also to operating room personnel having contact with the patient.

SUMMARY OF THE INVENTION

This invention provides a novel leakage current cancelling circuit that is utilized to cancel the R.F. leakage current that exists at either the patient or active electrodes of an electrosurgical instrument.

It is therefore an object of this invention to provide a novel leakage current cancelling circuit.

It is another object of this invention to provide a novel leakage current cancelling circuit that cancels the R.F. leakage current that exists at either the active or patient electrodes of an electrosurgical instrument.

It is still another object of this invention to provide a leakage current cancelling circuit that operates to prevent burns to a patient in contact with an electrode of an electrosurgical instrument.

It is yet another object of this invention to provide a leakage current cancelling circuit that is simple yet effective in accomplishing the intended purpose.

With these and other objects in the view, which will become apparent to one skilled in the art as the description proceeds, this invention resides in the novel construction, combination, and arrangement of parts substantially as hereinafter described, and more particularly defined by the appended claims, it being understood that such changes in the precise embodiments of the herein disclosed invention are meant to be included as come within the scope of the claims.

BRIEF DESCRIPTION OF THE DRAWINGS

The accompanying drawing illustrates two complete embodiments of the invention according to the best mode so far devised for the practical application of the principles thereof, and in which.

DESCRIPTION OF THE INVENTION

Figure 1:
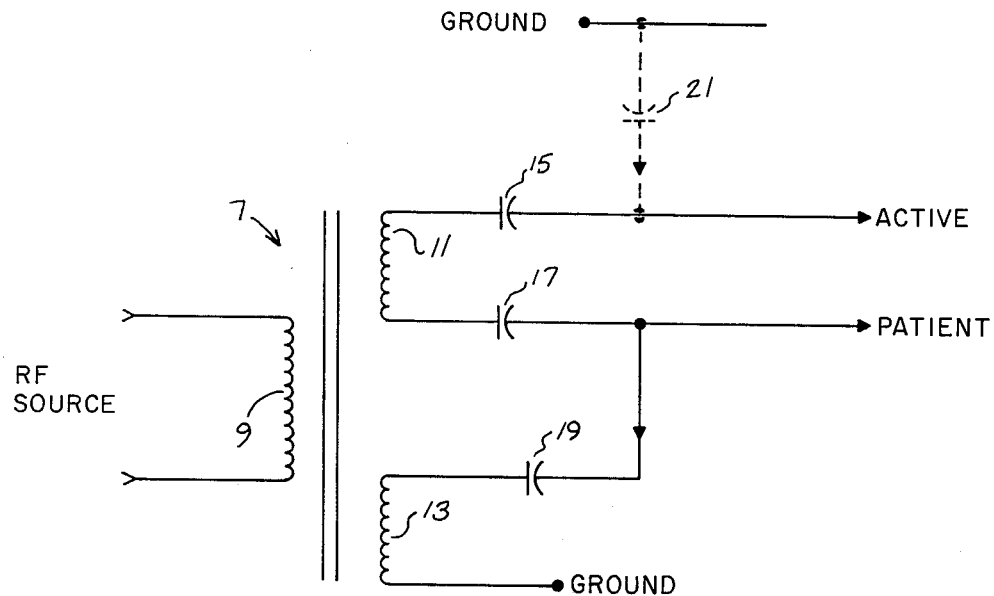
FIG. 1 is an electrical schematic circuit diagram of one embodiment of the leakage current cancelling circuit of this invention.

Referring now to the drawings, two embodiments for cancelling undesired leakage currents are shown. In the embodiment shown in FIG. 1, only the more critical patient leakage is cancelled, while the embodiment shown in FIG. 2 can operate to cancel leakage current in either the active side or the patient side of the output circuit.

The embodiment shown in FIG. 1 operates on the principle of addition of current to the patient connection of correct magnitude and phase to cancel the existing patient leakage current. As shown, the output power transformer 7 has a primary winding 9 connected with an R.F. source of current (not shown), and the isolated output to the active and patient electrodes of the electrosurgical instrument (not shown) is coupled from secondary winding 11 of the transformer. In addition, transformer 7 also has a tertiary winding 13. As is conventional, both sides of secondary winding 11 are connected with the active and patient electrodes through capacitors 15 and 17, respectively. As also shown in FIG. 1, tertiary winding 13 has one side connected with ground while the other side is connected to the patient side of the output circuit through capacitor 19. Finally, undesired leakage current is indicated as the total effective stray capacitance 21 extending between the active electrode and ground.

Thus, as can be seen from FIG. 1, the current to cancel the existing patient leakage current is taken from capacitor 19 in series with tertiary winding 13 of output transformer 7. The ratio of the number of turns of tertiary winding 13 and the secondary winding 11 of output transformer 7 and the value of capacitor 19 are selected so that the leakage current due to stray capacitance 21 minus the current through capacitor 19 and tertiary winding 13 is minimum.

If desired, capacitor 19 can be made variable and cancelling can then be applied with a servo loop (not shown) to automatically adjust the amount of current added to bring the voltage at the patient terminal near zero. An analog of this cancelling technique would be a capacitance bridge where the null detector is an ammeter in the patient lead to ground (not shown).

The leakage current cancelling circuit shown in FIG. 1 has been found advantageous for use since the current added can easily have the correct wave form and is produced by the same driving voltage which generates the undesired leakage current. In addition, low frequency sink current can easily be made small through the use of a small series capacitor and a high driving voltage. Also, the circuit of FIG. 1 is insensitive to operating frequency since the capacitively coupled currents are balanced with one another. A disadvantage of the circuit as shown in FIG. 1, however, is that since there is increased loading on the patient connector, there is an increased active leakage when the active side of the output circuit is grounded.

Figure 2:
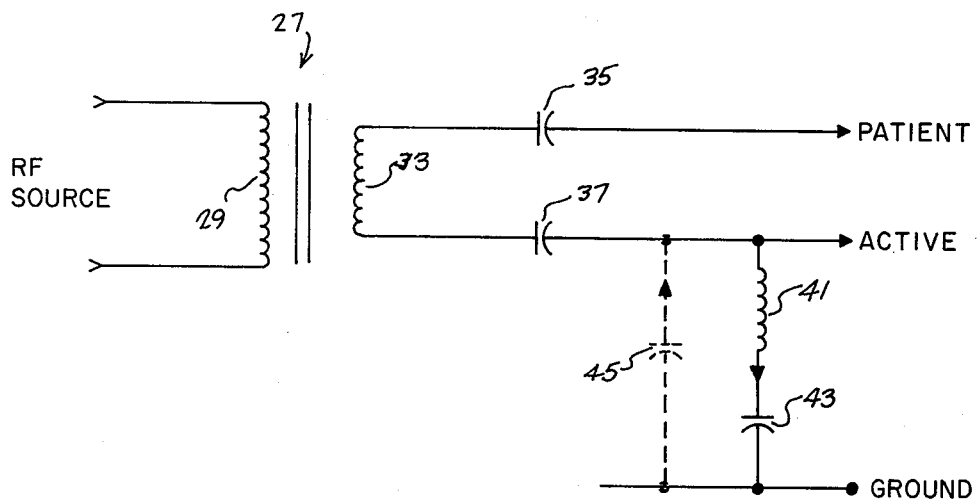
FIG. 2 is an electrical schematic circuit diagram of a second embodiment of the leakage current cancelling cirucit of this invention.

Referring now to FIG. 2, output transformer 27 has a primary winding 29 connected with an R.F. source of current (not shown) and a secondary winding 33 connected through capacitors 35 and 37 to the patient and active electrodes, respectively, of the electrosurgical instrument (not shown). The active side of the output circuit is connected with ground through series connected inductor 41 and capacitor 43, with inductor 41 and capacitor 43 being indicated to be in parallel with the total effective stray capacitance 45 of the circuit.

For the circuit of FIG. 2, inductor 41 of the series LC circuit, formed with capacitor 43, is chosen in conjunction with capacitor 37 so that inductor 41 and capacitors 37 and 43 form a pole of impedance at output fundamental frequency (0.5 megahertz has been utilized), the line frequency sink current is minimal, and the resulting circuit admittance pole lies well away from any of the admittance pole places so that it does not fall on or near a significant component. Inductor 41 is chosen so as to have as high a Q as is practical, and capacitor 43 and inductor 41 are selected for acceptably low low frequency sink current and so that the current due to the stray capacitance minus the current through the series LC circuit is acceptably low for all fundamental frequencies of concern.

The leakage current cancelling circuit of the embodiment shown in FIG. 2 has been found to be advantageous in that there is little increase in leakage current from the opposite output pole, but has been found to have disadvantages in that only the fundamental component will be effected if the current to be cancelled has a complex wave form, and in the creation of a difficulty in selecting capacitor 37 so as to attain acceptably low low frequency sink currents and at the same value placing the admittance pole far enough away from the impedence pole.

Overall, however, it has been found that the leakage current cancelling circuit of this invention provides an effective yet simple means for automatically cancelling undesired leakage currents.

What is claimed is:
1. The combination comprising:
  an electrosurgical instrument having an active electrode and a patient electrode;
  a power transformer having an isolated output circuit connected to said active and patient electrodes for supplying current thereto;
  means for supplying power to said power transformer; and,
  a leakage current cancelling circuit for use in cancelling leakage current at said isolated output circuit, said cancelling circuit comprising means for offsetting leakage current caused by stray capacitance to ground at said output circuit, said offsetting means including inductive and capacitive elements connected with one side of said output circuit and ground and having values selected to accomplish said leakage current cancellation.

2. The combination as claimed in claim 1 wherein said offsetting means includes a tertiary winding on said transformer and a capacitor connected in series with said tertiary winding, said capacitor being connected to said one side of said output circuit.

3. The combination as claimed in claim 2 wherein said one side of said output circuit includes the patient electrode of said electrosurgical instrument.

4. The combination as claimed in claim 1 wherein said offsetting means includes a series connected inductor and capacitor forming a series LC circuit connected between ground and said one side of said output circuit.

5. The combination as claimed in claim 1 wherein said one side of said output circuit includes the active electrode of said electrosurgical instrument.

6. In an electrosurgical unit having an electrosurgical instrument, an R.F. power source, and a transformer responsive to said R.F. power source, with said electrosurgical instrument having an active electrode and a patient electrode connected to said transformer by means of an isolated output circuit, the improvement comprising:
  a leakage current cancelling circuit for use in cancelling leakage current on the patient electrode side of said isolated output circuit, said leakage current cancelling circuit comprising;
  a first capacitor connected between said transformer and said patient electrode,
  a tertiary winding on said transformer one side of which is connected with ground, and
  a second capacitor connected at one side to the other side of said tertiary winding and at the other side between said first capacitor and said patient electrode whereby current of correct magnitude and phase are coupled to the patient side of said output circuit to cancel the existing leakage currents thereon.

7. In an electrosurgical unit having an electrosurgical instrument, an R.F. power source, and a transformer responsive to said R.F. power source, with said electrosurgical instrument having an active electrode and a patient electrode connected to said transformer by means of an isolated output circuit, the improvement comprising:
a leakage current cancelling circuit for use in cancelling leakage current on one side of said isolated output circuit, said leakage current cancelling circuit comprising:
a first capacitor connected between said transformer and one said electrodes;
a second capacitor one side of which is connected with ground; and
an inductor one side of which is connected with the other side of said second capacitor and the other side of which is connected between said first capacitor and said one of said electrodes whereby existing leakage currents on said one side of said output circuit are cancelled.

8. The leakage current cancelling circuit of claim 7 wherein the value of said inductor is such that it has as high a Q as is practical and in conjunction with said first capacitor such that said inductor and said first and second capacitors form a pole of impedance at the output fundamental frequency, the line frequency sink current is minimal, so that the resulting circuit admittance pole is spaced from any significant frequency component of the output waveform.

* * * * *

UNITED STATES PATENT AND TRADEMARK OFFICE
CERTIFICATE OF CORRECTION

PATENT NO. : 3,946,738
DATED : March 30, 1976
INVENTOR(S) : DAVID W. NEWTON and JOHN M. ADAN It is certified that error appears in the above—identified patent and that said Letters Patent are hereby corrected as shown below:

Insert name of assignee as follows:

VALLEYLAB, INC.

Boulder, Colorado 80301

Signed and Sealed this

Fourteenth Day of December 1976

[SEAL]

Attest:

RUTH C. MASON
Attesting Officer

C. MARSHALL DANN
Commissioner of Patents and Trademarks